United States Patent [19]

Buchbinder et al.

[11] Patent Number: 4,976,689

[45] Date of Patent: Dec. 11, 1990

[54] OUTER EXCHANGE CATHETER SYSTEM

[75] Inventors: Maurice Buchbinder; Ronald J. Solar, both of San Diego, Calif.

[73] Assignee: Medtronic Versaflex, Inc., Calif.

[21] Appl. No.: 267,047

[22] Filed: Nov. 4, 1988

Related U.S. Application Data

[63] Continuation of Ser. No. 235,829, Aug. 18, 1988, Pat. No. 4,944,740, which is a continuation of Ser. No. 909,446, Sep. 19, 1986, abandoned, which is a continuation-in-part of Ser. No. 651,806, Sep. 18, 1984, abandoned.

[51] Int. Cl.$^5$ ..................... A61M 29/02; A61M 25/00
[52] U.S. Cl. ..................................... 604/95; 604/164; 604/282; 606/194; 128/898
[58] Field of Search ................................. 604/95–103, 604/52, 53, 170, 280, 282; 128/344, 656–658, 898; 606/194

[56] References Cited

U.S. PATENT DOCUMENTS

| | | | |
|---|---|---|---|
| 2,688,329 | 9/1954 | Wallace | 604/95 |
| 4,044,765 | 8/1977 | Kline | 604/282 |
| 4,564,014 | 1/1986 | Fogarty et al. | |
| 4,582,181 | 4/1986 | Sampson | |
| 4,641,654 | 2/1987 | Sampson et al. | 604/95 |
| 4,661,094 | 4/1987 | Simpson | 604/280 |
| 4,664,657 | 5/1987 | Williamitis et al. | 604/265 |

Primary Examiner—Stephen C. Pellegrino
Attorney, Agent, or Firm—John L. Rooney

[57] ABSTRACT

This invention relates to corporeal catheters. More particularly, this invention relates to an outer exchange catheter system comprising an outer catheter sheath and at least one inner catheter having a control means, the outer catheter sheath extending less than the full length of each inner catheter and being slidable thereover. This invention also relates to the method of using this outer exchange catheter system.

33 Claims, 7 Drawing Sheets

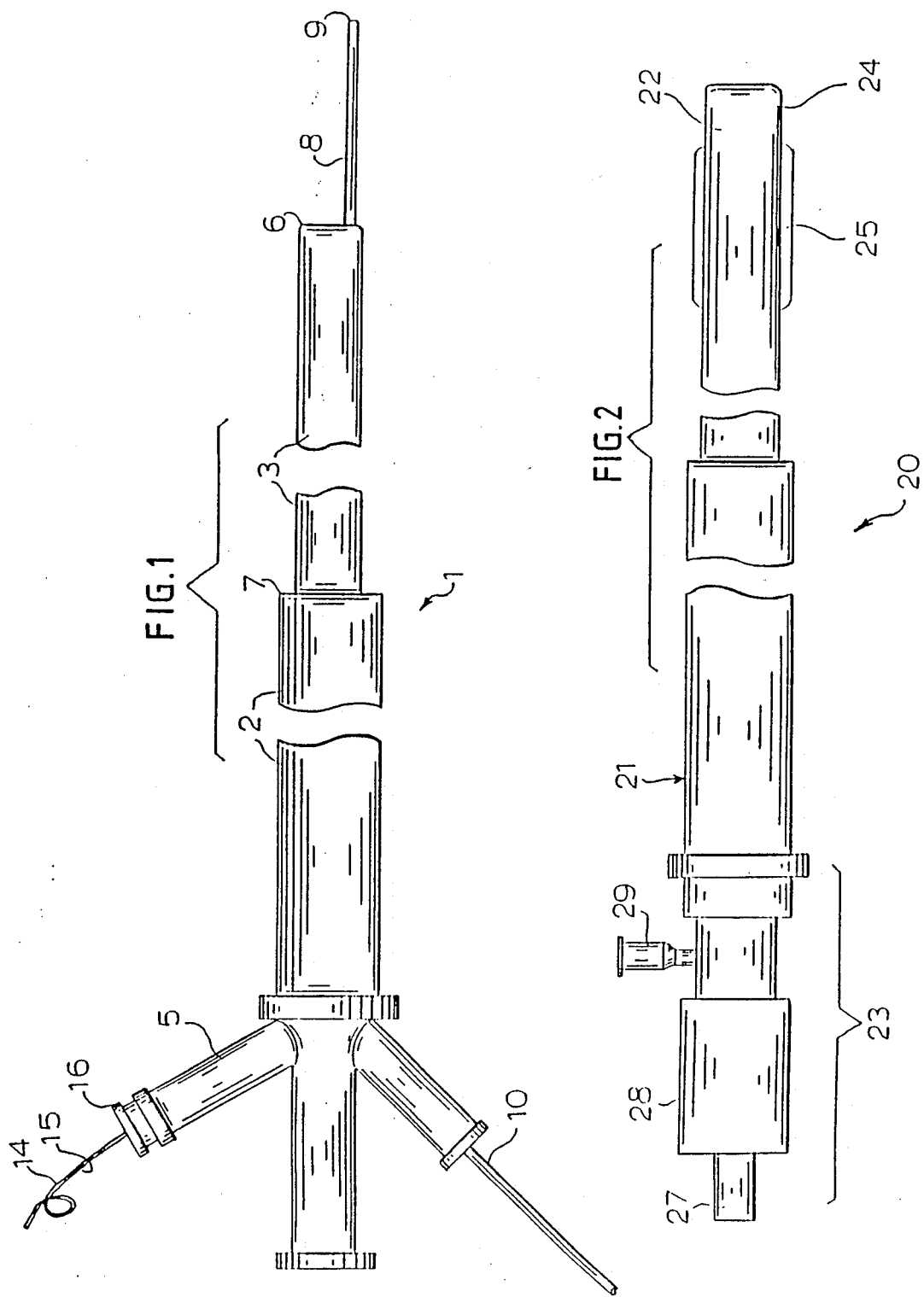

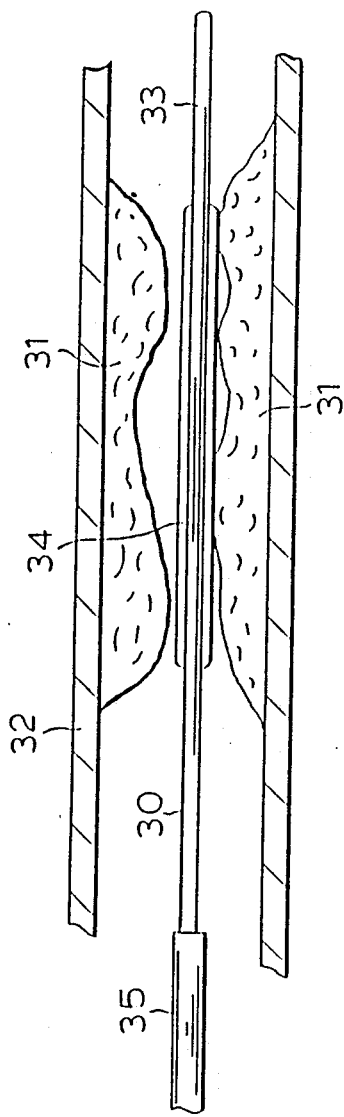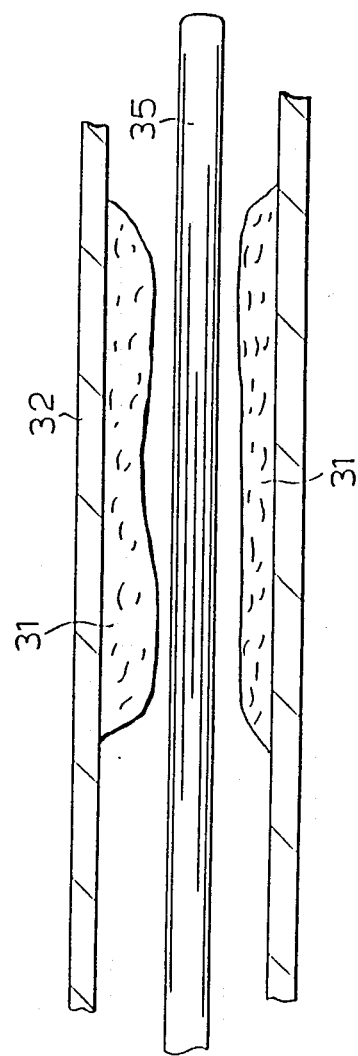

OUTER EXCHANGE CATHETER SYSTEM

CROSS-REFERENCE TO RELATED APPLICATIONS

This application is a continuation-in part of co-pending U.S. patent application Ser. No. 235,829, filed Aug. 18, 1988 now U.S. Pat. No. 4,944,740, which is a continuation of U.S. patent application Ser. No. 909,446, filed Sept. 19, 1986, now abandoned, which is a continuation-in-part of U.S. patent application Ser. No. 651,806, filed Sept. 18, 1984, now abandoned.

FIELD OF THE INVENTION

This invention relates to corporeal catheters. More particularly, this invention relates to a catheter system useful in cardiovascular applications wherein the catheter has a movable outer sheath to permit standard exchange techniques.

BACKGROUND OF THE INVENTION

Catheters comprise tube-like members that are inserted into the body for various medical reasons, some diagnostic and others therapeutic. While in many instances the steerability or directionality of such catheters is of concern, steerability is particularly important with regard to certain urological or cardiovascular applications.

There have been various attempts to develop steerable catheters. For example, U.S. Pat. No. 1,060,665 describes an early attempt to provide a catheter capable of some direction. However, the device disclosed in this patent, as well as catheters and catheter guides disclosed in later patents, such as U.S. Pat. Nos. 2,574,840 and 2,688,329, tend to be characterized by only limited directionality.

In addition, some supposedly steerable catheters are too large and rigid to be of practical use in cardiovascular techniques. See, for example, U.S. Pat. Nos. 3,470 876 and 3,605,725, where wires equidistantly positioned along the length of a catheter are connected to a steering means which pulls on the wires to cause the distal end of the catheter to go in a desired direction. Moreover, U.S. Pat. Nos. 3,521,620, 3,547,103, 3,625,200, and 4,020,829 describe coil spring guide wires that have a certain degree of directionality but are too rigid for safe usage in certain delicate cardiovascular procedures.

According to U.S. Pat. No. 4,033,331, a coronary catheter has a main lumen and a shaping wire lumen. When the wire is withdrawn through the shaping wire lumen, the catheter assumes certain predetermined configurations. While this so-called steerable catheter is useful in some cardiovascular applications, such as positioning the initial guiding catheter guide through which other devices are guided, its limited directionality and limited tip control preclude extensive use.

A medical procedure known as percutaneous transluminal coronary angioplasty (PTCA) was developed in approximately 1976-1977 by Dr. Andreas Grüntzig According to this procedure, blockage in a coronary artery can be reduced by positioning a balloon dilatation catheter across the blockage and inflating the balloon, which causes the blockage to decrease. Such positioning requires that the balloon dilatation catheter be "steered" into place, that is, across the stenotic lesion causing the blockage, by manipulation at the proximal end of the catheter The procedure is actually somewhat complex, consisting of introducing a catheter system via the femoral or brachial artery under local anesthesia. A pre-shaped guiding catheter is positioned into the orifice of the coronary artery, and through this guiding catheter a second dilatation catheter is advanced into the branches of the coronary artery. The dilatation catheter has an elliptically shaped balloon portion near the tip which can be inflated and deflated After traversal of the stenotic lesion of the coronary artery, the balloon portion is inflated with fluid, which dilates the lumen of the vessel.

The PTCA procedure and equipment have become increasingly refined over the past six years. The first marketable PTCA apparatus consisted of a small catheter with a single balloon port and no central lumen, that is, a so-called "fixed wire" system, which terminated in lateral openings at the distal end thereof This system, which is the subject of U.S. Pat. No. 4,195,637, was designed by Dr. Grüntzig and was marketed in the U.S. by USCI. The fixed wire catheter system disclosed in U.S. Pat. No. 4,195,637 comprises a balloon dilatation catheter and a low friction guide catheter consisting of one tubular member fitted into a more rigid, shrunk-on tubular member that is not co-extensive the distal end of the balloon dilatation catheter has a flexible tip advantageously fabricated from a spring steel wire.

In 1980-1981 Dr. John Simpson, working at Stanford University, began to modify the fixed wire system and eventually developed a catheter with a free central lumen for movable guide wires. This catheter system is the subject of U.S. Pat. No. 4,323,071, which is assigned to Advanced Cardiovascular Systems, Inc. (ACS), formerly known as Advanced Catheter Systems, Inc. By use of such a movable wire system, one could more readily select the desired coronary artery and reach smaller branches since the movable guidewires are inherently smaller and more flexible than the fixed wire system. Movable guidewires are particularly useful in a technique known as catheter exchange, whereby one catheter positioned concentrically around a guidewire is replaced by, i.e., exchanged for, another such catheter, the guidewire maintaining the desired position. Subsequent to the development of the catheter with movable guidewires, known as the Simpson-Robert system and marketed by ACS, USCI has abandoned the fixed wire system and has marketed a similar device, calling it the steerable catheter, DILACA ®.

Samson, U.S. Pat. No. 4,516,972 issued May 14, 1985, to ACS. This patent: is directed to a guide catheter having a helically wound ribbon of flexible material imbedded in the wall of the catheter to provide torsional rigidity.

There is a further catheter system in use known as the Hartzler low profile catheter system. According to this catheter system a balloon dilatation catheter has a concentrically contained guidewire extending the length of said catheter. Moreover, the distal end of the guidewire extends a short distance beyond the distal end of the balloon dilatation catheter and is affixed to the distal end of the balloon dilatation catheter.

The catheter system with movable guidewires and the low profile catheter system each represent an advance but still have disadvantages such as limited steerability, which is at present dependent upon the torquability, or torque control, of the movable wire. Steerability is highly significant in a cardiovascular procedure such as PTCA, or angioplasty, because less steerability results in greater time spent in the body and more possible patient trauma. Multiple insertions of guidewires and catheters can lead to thrombosis in that coagulation may commence along a guidewire surface and be forced into the heart when a catheter is slid over the guidewire. Furthermore, there are some blockages which simply cannot be reached with presently known equipment.

Co-pending U.S. patent application Ser. No. 193,201 filed May 9, 1988, and U.S. patent application Ser. No. 213,662, filed June 30,1988, and U.S. Pat. No. 4,723,936, all of which are incorporated herein by reference, are directed to improved steerable catheter means useful in, for example, cardiovascular applications. The catheter means disclosed therein are characterized by a relatively low profile and enhanced directionality due to combined rotation of the catheter means and active deflection of the catheter tip.

As mentioned above, PTCA technology appears to be directed toward fixed wire dilatation catheters, especially low profile catheters To achieve such low profiles, it has been necessary to abandon the through lumen of the movable guidewire catheter, a design change which has precluded standard exchange techniques wherein dilatation balloons are changed over a guidewire. In addition, a guidewire cannot be maintained in position across and past a stenosis once dilatation is complete because as soon as a fixed wire catheter is withdrawn, the position across and beyond the stenosis is lost.

OBJECTS OF THE INVENTION

It is an object of the invention to provide an improved catheter system.

It is also an object of the invention to provide a catheter system useful in cardiovascular applications wherein the catheter has a movable outer sheath to permit standard exchange techniques.

It is a further object of the invention to provide a method for cardiovascular techniques wherein a movable outer sheath is positioned adjacent to or across a stenosis.

These and other objects of the invention will become more apparent in the discussion below.

BRIEF DESCRIPTION OF THE DRAWINGS

FIGS. 1 and 2 each represent a planar view of an embodiment of the invention;

FIG. 3 represents a partially sectional view of an embodiment of the invention where a balloon dilatation catheter has been positioned across a stenosis in an artery;

FIG. 4 represents a partially sectional view of FIG. 3 after dilatation of the stenosis and advancement of the outer sheath;

DETAILED DESCRIPTION OF THE INVENTION

Figure 5:
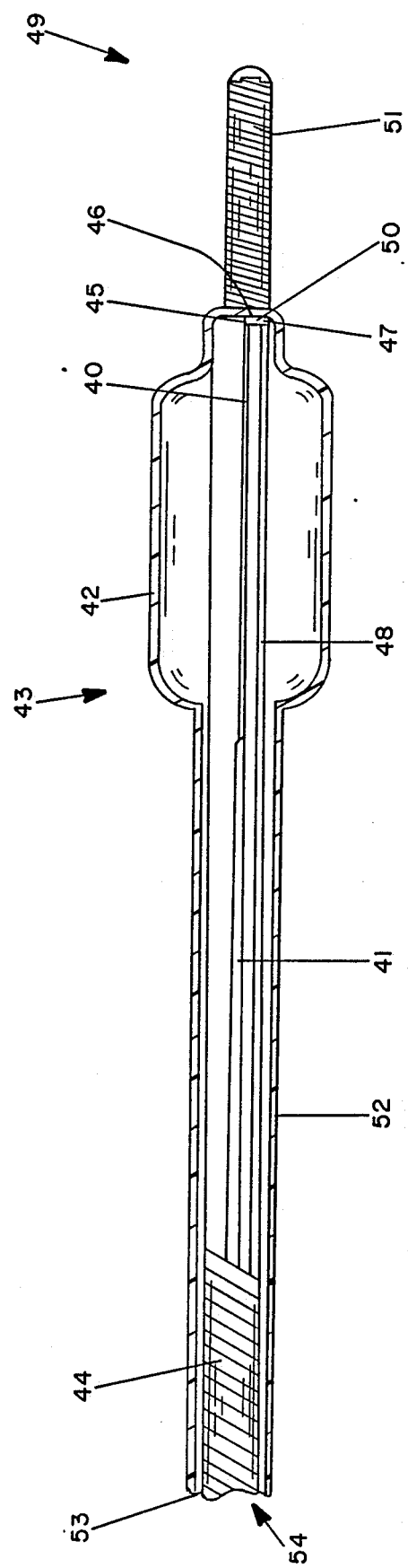
FIGS. 5 and 6 each represent a partly cross-sectional planar view of the distal portion of a balloon dilatation catheter having a spring coil body.

Applicants have surprisingly developed a flexible and steerable catheter means, or delivery means, which is more useful than those known. According to the invention, a catheter means comprises a catheter, such as a fixed wire, steerable catheter, having a sleeve, an outer shell or sheath, which facilitates exchange capabilities. The sleeve extends from the proximal end of the catheter to a point approximately one-third from the distal end of the catheter, i.e., it covers about two-thirds of the catheter. In this arrangement, the sheath can slide easily and freely over the catheter and, if desired, be advanced over the distal end of the catheter.

This invention is especially intended for use with a dilatation catheter or dilatation catheter system wherein the distal end comprises dilatation balloon means to be placed across a stenosis. The sheath can be positioned adjacent to the stenosis to provide support to the dilatation catheter for crossing the stenosis. Once a stenosis has been crossed and dilated with the dilatation balloon, the dilatation catheter can be withdrawn, leaving the sheath adjacent to the stenosis and an additional catheter, for example, a second dilatation catheter, a fiber optic viewing catheter, an arterial stent delivery catheter, or the like, may easily be advanced through the sheath to the stenosis. In addition, the sheath may also be advanced over the distal tip of the dilatation catheter beyond the stenosis Use of the system in this manner would be applicable in a situation where the desired dilatation effect was not achieved. For example, once a dilatation balloon of lowest available profile has crossed the stenosis and dilatation has taken place, the sheath being in retracted position, the sheath is then advanced or slid over the tip of the dilatation catheter beyond the area of stenosis. The catheter can then be withdrawn, leaving the outer sheath across and beyond the stenosis. A larger dilatation balloon could then be introduced. The introduction of a larger balloon, or the exchange from a smaller to a larger balloon, would be much simpler than over a wire since the sheath is already in place across and beyond the area of stenosis, and the only maneuver the operator has to perform is to advance the dilatation balloon of desired size inside the sheath.

The sheath could also act as a coronary shunt in the event of abrupt closure of a vessel. In such a case, the dilatation catheter will be pulled out, the sheath alone being maintained beyond the area of complete occlusion. This would provide flow distally, similar to the ACS reperfusion catheter concept.

With such a system as described above, distal pressure beyond the area of stenosis could theoretically be measured, for example, with a pressure sensing membrane at the distal end of an optical fiber or with a pressure transducer at the proximal end of the outer sheath. Also, with the dilatation catheter removed, distal dye could be injected to inspect the degree of stenosis and the arterial flow beyond the site dilated, or other agents such as localized thrombolytic agents, vasodilators, or the like, could be injected.

It should be noted that the so-called outer exchange sleeve or sheath does not alter the profile of the catheter since it does not extend all the way to the distal tip of the dilatation catheter or over the dilatation balloon. In retracted position it is approximately one-third of the way from the distal tip, and it is advanced over the dilatation balloon only when needed.

Another aspect of this invention is that the presence of the outer sheath can improve the efficacy of a catheter such as a dilatation catheter. It is believed that the outer sheath in some manner improves the effectiveness and/or maneuverability of certain dilatation catheters due to any stiffness or support provided, that is, additional support for the catheters enable them to negotiate tortuous paths and cross tight stenoses.

With respect to exchanging catheters, the exchange would be accomplished according to the invention in a less traumatic manner than current technology allows. Presently, catheter exchange takes place over a guidewire, a very time-consuming process (about 15 minutes), which requires additional fluoroscopic exposure. The guidewire is first exchanged for a longer "exchange wire," which exchange carries the risk of thromboembolism. Next, the balloon dilatation catheter is withdrawn, and it rubs against the lining of the artery (the intima). This could result in intimal damage (denudation of the endothelial layer), which may subsequently cause thrombus formation (clot). After the first catheter is removed, a second dilatation catheter is passed over the exchange wire, and once again this may result in intimal damage. Thus, each catheter exchange results in two additional passes of the catheter against the arterial lining, and the more the intima is "roughed", the greater is the chance of thrombolic complications.

With the outer sheath design herein, catheter exchanges take place within the sheath, i.e., the "exchanged" catheters do not touch the arterial wall during passage. Moreover, a set of calibrated marks may be on the catheter and sheath so that insertion of subsequent catheters can be done without fluoroscopy (less radiation exposure and dye injection).

According to the invention, a stenosis in a passageway in a body is dilated by a method which comprises:

(a) introducing a guide catheter having proximal and distal ends and a single lumen into the body through an incision or opening;

(b) advancing a catheter system comprising an outer sheath and a first inner dilatation catheter system, each of said outer sheath and said first dilatation catheter system having proximal and distal ends and said first dilatation catheter system having first dilatation balloon means adjacent the distal end thereof, into and through the guide catheter to cause said first dilatation balloon means to be positioned across a stenosis in said passageway, the distal end of the sheath preferably being adjacent the stenosis;

(c) inflating said first dilatation balloon means to cause the stenosis to dilate;

(d) deflating said first dilatation balloon means;

(e) withdrawing said first dilatation catheter system in the proximal direction;

(f) advancing a second dilatation catheter system having proximal and distal ends and second, larger dilatation balloon means distally within said outer sheath to cause the larger balloon dilatation means to be positioned across said stenosis;

(g) inflating said second balloon dilatation means; and (h) repeating steps (d) to (g) until the stenosis is sufficiently dilated.

In one embodiment of the invention, after deflation of the dilatation balloon means the outer sheath is slidably advanced along the dilatation catheter system to position the outer sheath across the stenosis. Then, after withdrawal of the first dilatation catheter system and advancement of the second dilatation catheter, the second dilatation catheter is positioned across the stenosis, and the outer sheath is withdrawn in the proximal direction to position the distal end of the outer sheath near the distal end of the second dilatation catheter or, preferably, to position the distal end of the outer sheath adjacent the stenosis. Also, in repeating the steps of the invention, in one or more sequences of steps the outer sheath would be positioned across the stenosis during withdrawal and in one or more other sequences the outer sheath would remain adjacent the stenosis during withdrawal.

Furthermore, it is within the scope of the invention that, dependent upon the course of the procedure and the equipment available to or preferred by the cardiologist user, a second catheter system and/or a guidewire may be advanced into the outer sheath and across the stenosis in step (f), as repeated. For example, after the first catheter is withdrawn, a guidewire may be advanced through the outer sheath, and then an "over-the-wire" balloon dilatation catheter would be advanced through the outer sheath and over the guidewire, into position across the stenosis. Also, in some applications a catheter not having a balloon dilatation means may be advanced through the outer sheath, either alone or over a guidewire.

Thus, the method herein could comprise procedures wherein different catheter and/or guidewire devices are advanced through the outer sheath in varying order. In another embodiment of the invention, an outer sheath and a guidewire encompassed thereby would be advanced through the guide catheter to a position adjacent the stenosis. The guidewire is then advanced across the stenosis so that the distal end of the guidewire is distal to the stenosis, after which a balloon dilatation catheter is advanced over the guidewire to position the deflated dilatation balloon across the stenosis. After inflation and then deflation of the balloon, the balloon dilatation catheter is withdrawn. This procedure can be repeated or varied as necessary. Also, in a variation of the above procedure, the distal end of the guidewire remains proximally adjacent to the stenosis as the balloon dilatation catheter is advanced across the stenosis According to a further embodiment of the invention, the outer sheath and guidewire are advanced through the guide catheter to a position proximal to the stenosis, and then the guidewire is withdrawn. After such withdrawal a fixed wire balloon dilatation catheter is advanced through the outer sheath and across the stenosis, so that the dilatation balloon is positioned across the stenosis. After inflation and deflation of the dilatation balloon, the balloon dilatation catheter is withdrawn. The balloon dilatation catheter itself may be either steerable or non-steerable.

As mentioned above, the invention herein is directed to an outer exchange catheter system whereby a catheter such as a dilatation catheter has an outer sheath. More particularly, such catheter systems comprise:

an outer flexible catheter sheath having distal and proximal ends, and at least one inner flexible catheter having distal and proximal ends and one or more lumens, each inner catheter extending through the outer catheter sheath and being slidable therein, and the distal end of each inner catheter protruding substantially beyond the distal end of the outer catheter sheath.

In another embodiment of the invention, such catheter systems comprise:

an outer flexible catheter sheath having distal and proximal ends, at least one inner flexible catheter having distal and proximal ends and one or more lumens, each inner catheter extending through the outer catheter sheath and being slidable therein, and the distal end of each inner catheter protruding substantially beyond the distal end of the outer catheter shell, and at least one inner catheter having one of said lumens closed at its distal end, a deflection or steering wire having distal and proximal ends and extending the length of said inner catheter through the lumen having the closed end, the distal end of the deflection wire being embedded in said closed end, and control means attached to the proximal end of at least one inner catheter.

The proximal end of the deflection wire extends through such control means, and the control means has an engaging means which fixedly engages said deflection wire to cause the deflection wire to longitudinally displace either toward or away from the distal end thereof, said displacement causing the distal end of the inner catheter to bend out of or toward the line of the longitudinal axis of the inner catheter. The control means can be rotated to cause the distal end of an inner catheter to rotate.

The open lumens within an inner catheter may carry various objects and/or function as other than mere conduits for such objects. For example, an open lumen may contain a fixed or movable guidewire, a retractable pressure sensing fiber, or an inflatable dilatation balloon. Also, radiopaque fluids or active substances may be transmitted through a lumen, or a lumen itself may be used as a pressure sensing means.

An inner flexible catheter can be virtually any of the known dilatation catheters, including, but not limited to, the catheters described above. This invention is especially directed to the catheters and catheter systems described in the aforementioned U.S. patent applications Ser. Nos 193,201 and 213,662 and U.S. Pat. No. 4,723,936, specifically incorporated herein by reference with regard to the dimensions, materials, and construction of said catheters.

In additional embodiments of the invention, an inner catheter may comprise:

(A) a flexible catheter having distal and proximal ends and one or more lumens extending therethrough, at least one of said lumens being closed at its distal end, a deflection wire having distal and proximal ends and extending the length of a lumen having a closed end, the distal end of the deflection wire being embedded in said closed end, and control means attached to the proximal end of the catheter, the proximal end of the deflection wire extending to or through the control means and the control means having an engaging means which fixedly engages said deflection wire to cause the deflection wire to longitudinally displace either toward or away from the distal end thereof, said displacement causing the distal end of the inner catheter to bend out of or toward the line of the longitudinal axis of the catheter, and the control means being capable of being rotated such that the distal end of the catheter rotates;

(B) a flexible catheter comprising a spring coil body defining a lumen, each of said catheter and said spring coil body having proximal and distal ends, the distal end of said spring coil body being closed, and said spring coil body having a flexible covering thereon, dilatation balloon means positioned concentrically around the distal end of said spring coil body, a deflection wire having proximal and distal ends being substantially co-extensive with said spring coil body, the distal end of said deflection wire being attached to the distal end of said spring coil body, and control means attached to the proximal end of said catheter, the proximal end of said deflection wire extending to or through the control means, the control means having engaging means which fixedly engages the proximal end of said deflection wire to cause said deflection wire to be displaced distally or proximally, said displacement causing the distal end of said catheter to bend out of or toward the line of its longitudinal axis, and the control means having rotation means capable of causing said catheter to rotate about its longitudinal axis;

(C) a flexible catheter comprising a spring coil body defining a lumen, each of said catheter and said spring coil body having proximal and distal ends, the distal end of said spring coil body being closed, and said spring coil body having a flexible covering thereon, dilatation balloon means positioned concentrically around the distal end of said spring coil body, and control means attached to the proximal end of said catheter, said control means having rotating means capable of causing said catheter to rotate about its longitudinal axis;

(D) a flexible catheter comprising a spring coil body defining a lumen, said spring coil body having proximal and distal ends, a flexible tip having proximal and distal ends, the proximal end of said flexible tip being positioned a short distance from the distal end of said spring coil body to form a discontinuity, and a flexible covering, said flexible covering extending from the proximal end of said spring coil body along the length of said spring coil body across said discontinuity to the proximal end of said proximal tip, a dilatation balloon means positioned around said discontinuity, a deflection wire having proximal and distal ends, said deflection wire extending substantially co-extensively with said spring coil body, the distal end of said deflection wire being attached to the proximal end of said flexible tip, and control means having engaging means which fixedly engages the proximal end of said deflection wire to cause said deflection wire to be displaced distally or proximally, said displacement causing the distal end of said catheter to bend out of or toward the line of its longitudinal axis, and the control means being capable of causing said catheter to rotate about its longitudinal axis;

(E) a flexible catheter comprising a spring coil body defining a lumen, each of said catheter and said spring coil body having proximal and distal ends, the distal end of said spring coil body being open, a deflection wire having proximal and distal ends and being substantially co-extensive with said spring coil body, the distal end of said deflection wire being attached to the distal end of said spring coil body, and control means attached to the proximal end of said catheter, the proximal end of said deflection wire extending to or through the control means, the control means having engaging means which fixedly engages the proximal end of said deflection wire to cause said deflection wire to be displaced distally or proximally, said displacement causing the distal end of said catheter to bend out of or toward the line of its longitudinal axis, and the control means being capable of causing said catheter to rotate about its longitudinal axis; or (F) a flexible catheter comprising a spring coil body defining a lumen, each of said catheter and said spring coil body having proximal and distal ends, the distal end of said spring coil body being open, and said spring coil body having a flexible covering thereon, and control means attached to the proximal end of said catheter, said control means being capable of causing said catheter to rotate about its longitudinal axis.

In addition, in one or more sequences of the invention a guidewire may be positioned across a stenosis to facilitate subsequent positioning of a catheter. Also, in some instances an inner catheter may comprise a guidewire member.

The invention can perhaps be better understood by making reference to the drawings In FIG. 1, catheter system 1 is essentially comprised of outer catheter sheath or shell 2, inner catheter 3, deflection wire 4, and control means 5. Outer sheath 2 encloses a substantial portion of inner catheter 3, from about 40% to 90%, preferably from about 55% to 75%, of inner catheter 3. Inner catheter 3 is freely rotatable and slidable within outer sheath 2. Distal end 6 of inner catheter 3 projects out of the distal end 7 of outer sheath 2.

A movably controlled, i.e., movable or steerable, guidewire 8 extends the length of catheter system 1, the distal end 9 of guidewire 8 projecting out of inner catheter 3 and the proximal end 10 of guidewire 8 extending through control means 5. Inner catheter 3 may have, for example, two lumens, one open lumen through which movable guidewire 8 is introduced, and a lumen in which the distal end is closed. The distal end of deflection wire 4 would be embedded from about 0.1 to 7 centimeters, preferably from about 1 to 5 centimeters, into said closed distal end.

The proximal end 15 of deflection wire 4 may extend into or through control means 5 and be fixedly held by engaging means 16. Turning engaging means 16 causes wire 4 to shorten or lengthen relative to inner catheter 3, which in turn causes distal end 6 of inner catheter 3 to bend toward or away from the longitudinal axis of outer sheath 2 and inner catheter 3.

The embodiment of the invention shown in FIG. 2 comprises a catheter system 20 essentially comprised of outer sheath 21, inner catheter 22, and control means 23. Inner catheter 22 is fully rotatable and/or slidable within outer sheath 21. Distal end 24 of inner catheter 22 comprises dilatation balloon means 25, shown in deflated position.

The proximal portion (not shown) of inner catheter 22 is connected to the distal portion of control means 23. Also, catheter 22 has a deflection wire therein (not shown) which is connected to engaging means (not shown) within control means 23. Turning control knob 27 causes the deflection wire to move longitudinally, which in turn causes the distal end 24 of inner catheter 23 to deflect, and rotation of annular surface 28 causes distal end 24 to rotate.

Inflation port 29 is in fluid communication with dilatation balloon means 25. In an alternative arrangement, inflation port 29 may be arranged concentrically around the longitudinal axis of control knob 27.

FIG. 3 shows an embodiment of the invention wherein a balloon dilatation catheter 30 has been advanced across a stenosis 31. The distal end 33 of the catheter is distal to stenosis 31, and the dilatation balloon 34 is positioned across the stenosis itself Outer sheath 35 is proximal to the stenosis.

After dilatation, outer sheath 35 is left in position while dilatation catheter 30 is withdrawn. A second catheter (not shown) can then be inserted through outer sheath 35 and positioned across the stenosis as in FIG. 3. In another embodiment of the invention shown in FIG. 4, the distal end of outer sheath 35 is advanced across and distal to the stenosis 31 and remains in that position while the balloon dilatation catheter 30 is withdrawn and a second catheter is optionally inserted.

In another embodiment of the invention, the outer sheath itself or the outer sheath in combination with a guidewire, preferably steerable, could be positioned adjacent to the stenosis. Then, if no guidewire is present or if the guidewire is withdrawn, a dilatation catheter, preferably a fixed wire dilatation catheter, could be inserted through the outer sheath and across the stenosis If a guidewire remains positioned across the stenosis, an "over the wire" dilatation catheter could be threaded along the guidewire and across the stenosis.

In FIG. 5, a tapered section 40 of a deflection wire 41 is located at a balloon section 42 of a catheter, generally designated as 43, having a spring coil body 44. This configuration will result in preferential bending of the catheter 43 at the balloon section 42 when a tip deflecting control means is activated, i.e., when longitudinal forces are applied to the proximal end (not shown) of deflection wire 41. The distal end of the spring coil body 44 is closed at closure 45, which closure may be a weld, a cap, solder, a braze, or, preferably, an adhesive such as a U.V. curing adhesive or cyano-acrylate bond. The distal end 46 of the deflection wire 41 is bonded to closure 45 or to the interior surface of the distal end 47 of the spring coil body 44 by suitable means, e.g., mechanical means, adhesive, solder, braze, or weld. An anchor wire or safety wire 48 may optionally be included, as shown in FIG. 5. Anchor wire 48 may provide more pronounced bending or facilitate the return of the distal end or tip 49 of the catheter 43 to a straight position.

The anchor wire 48, which is bonded to the spring coil body 44 at its proximal end (not shown) and its distal end 50, respectively, may be made from any metal wire, preferably a high tensile strength circular wire of stainless steel having a diameter of from about 0.001 to 0.020 in. Optionally this wire may have a rectangular cross-section of from about 0.001 to 0.020 in. x from about 0.001 to 0.040 in. Regardless of the shape of the cross-section, the distal end of the anchor wire 48 may be tapered, for example, to a diameter of from about 0.001 to 0.010.

Anchor wire 48 may optionally terminate at a point proximal from the distal end 50 of spring coil body 44. For example, the anchor wire 48 may terminate within spring coil body 44 at a point immediately proximal to the proximal portion of balloon section 42. The distal portion of the anchor wire 48 would then be bonded by suitable means, e.g., mechanical means, adhesive, solder, braze, or weld, to the interior surface of spring coil body 44.

To minimize vessel trauma and to facilitate catheter passage, the distal end 49 of the catheter 43 may have a spring guide tip 51, which is affixed or otherwise embedded in closure 45. The guide tip 51 may be made from any suitable metal or plastic coil spring having a diameter of from about 0.005 to 0.500 in. A material opaque to x-rays, e.g., platinum, gold, tungsten, tantalum, or the like, is preferred since the guide tip 51 would then act as a fluoroscopic marker to aid in precise positioning of the balloon section 42 of the catheter 43.

To allow the catheter to infuse fluids or hold pressure, for example, in the case of inflating a dilatation balloon, the spring coil body 44 is covered with an impervious body skin or tubing 52. The body skin 52 may comprise one or more layers of suitable low friction polymeric material such as a polyolefin, a polytetrafluoroethylene such as TEFLON ®, polyvinyl chloride, or the like, and may be applied by any one of a variety of methods known to those skilled in the art. For example, heat shrinkable tubing may be heat shrunk onto the spring coil body 44; polymeric material may be sprayed on or coextruded; or a tube of body skin may simply be slid over the spring coil body 44. Heat shrinking heat shrinkable tubing is preferred.

For the dilatation catheters described herein, the body skin 52 may be integral with the balloon section 42, and the balloon section 42 may be suitably bonded to the body skin 52. In use, the balloon section 42 would be inflated via a space 53 between the spring coil body 44 and body skin 52 or, preferably, via the lumen 54 formed by the spring coil body 44.

According to an embodiment of the invention not shown, the catheter may have an inner coating or skin extending substantially from the proximal end of the spring coil body 44 to the distal end 50 thereof, and a second, outer coating forming balloon section 42. The outer coating would not necessarily be co-extensive wit the inner coating and might extend distally and proximally from balloon section 42 only to the extent necessary to form an appropriate seal with the inner coating. The inner coating would then require an opening in the area of balloon section 42 for inflation or deflation thereof.

FIG. 5 represents an embodiment of the invention having the deflection wire 41 located within the lumen 54 of the spring coil body 44. Alternatively, deflection wire 41 could be located between the spring coil body 44 and the body skin 52, and an optical fiber having a pressure sensing membrane at its distal end could optionally be employed. If an anchor wire is employed, it could be located either within lumen 54 or between the spring coil body 44 and the body skin 52.

As mentioned above, the spring coil body terminates in a closure means. When no guide tip is present, the closure means may comprise a mass of adhesive having a substantially semispherical or rounded shape in the distal direction. Also, the closure means could have a polymeric covering which functions as an atraumatic tip. In any event, the distal end of the catheter of this type should be soft or low friction, or both.

Figure 6:
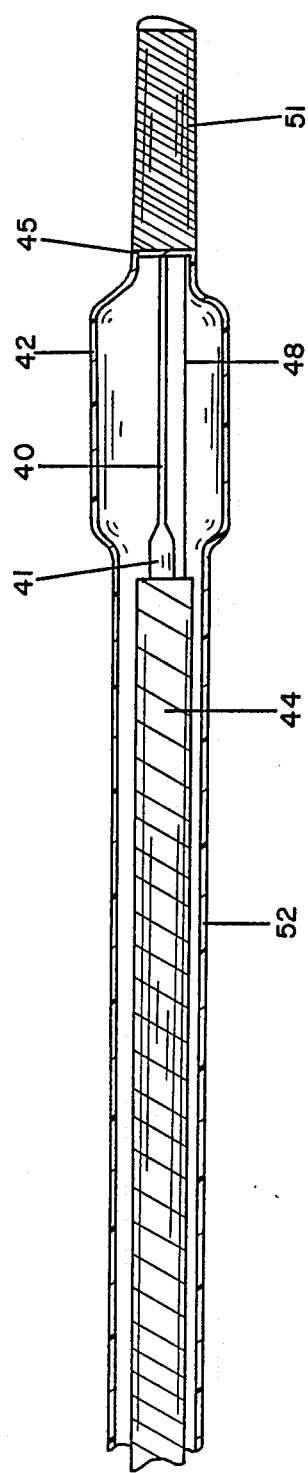

A further embodiment of a catheter useful according to the invention is shown in FIG. 6. In this configuration the spring coil body 44 terminates proximally to the balloon section 42 such that only the tapered section 40 of the deflection wire 41, and optionally the fine anchor wire 48 and/or an optical fiber (not shown), is within the balloon section 42. Since the mass of material within the balloon is reduced as compared to, for example, the embodiment shown in FIG. 5, the deflated diameter or profile of the balloon section may be smaller. This will allow for passage through smaller strictures. The anchor wire 48 may be deleted altogether or it may be positioned between the spring coil body 44 and the body skin 52.

Figure 7:
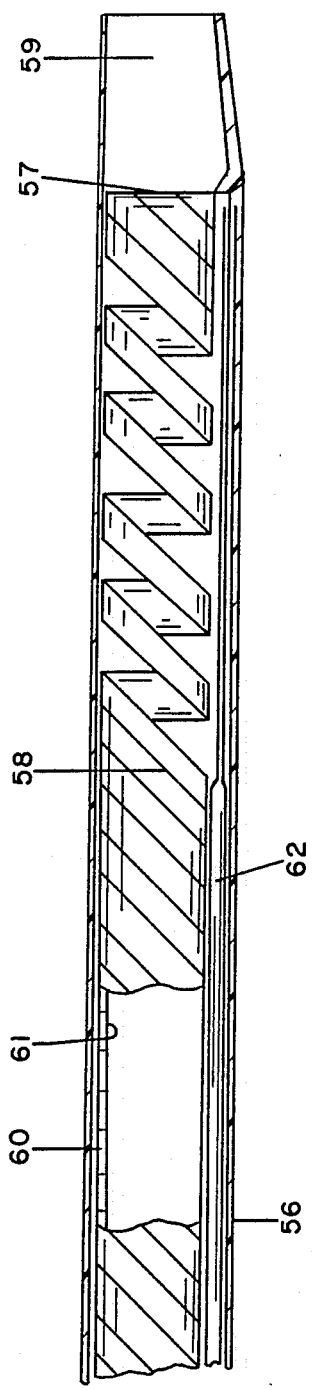
FIG. 7 represents a partly cross-sectional planar view of the distal portion of a catheter having a spring coil body.

A yet further embodiment of the invention is shown in FIG. 7. The steering mechanism is similar to that of the device represented in FIG. 5, although the device depicted in FIG. 7 has additional intended uses. Whereas FIG. 5 shows a device intended for stricture dilatation, that shown in FIG. 7 may be used for the delivery of other devices, e.g., catheters, guidewires, fiber optics, lasers, etc., and infusion of fluids, e.g., pharmaceuticals, radiopaque contrast agents, etc., to perform various diagnostic and therapeutic procedures.

The steering means for the embodiment shown in FIG. 7 has been described above. The body skin 56 extends beyond the distal end 57 of the spring coil body 58 to provide a soft, atraumatic, annular, i.e., cylindrical, tip 59, preferably made from a polytetrafluoroethylene such as TEFLON or another low friction polymeric material. An optional liner 60 provides a smooth surface for passage of other devices, such as mentioned above. The liner 60 is preferably made from TEFLON or another low friction polymeric material. The inner surface 61 of the liner 60 may be treated or grafted to improve lubrication, i.e., to reduce friction. This embodiment may optionally include an anchor wire (not shown) and/or an optical fiber (not shown) between the spring coil body 58 and the body skin 56. In addition, this embodiment may exclude deflection wire 41 and/or include balloon dilatation means (not shown) positioned concentrically around the distal portion of spring coil body 58.

Figure 8:
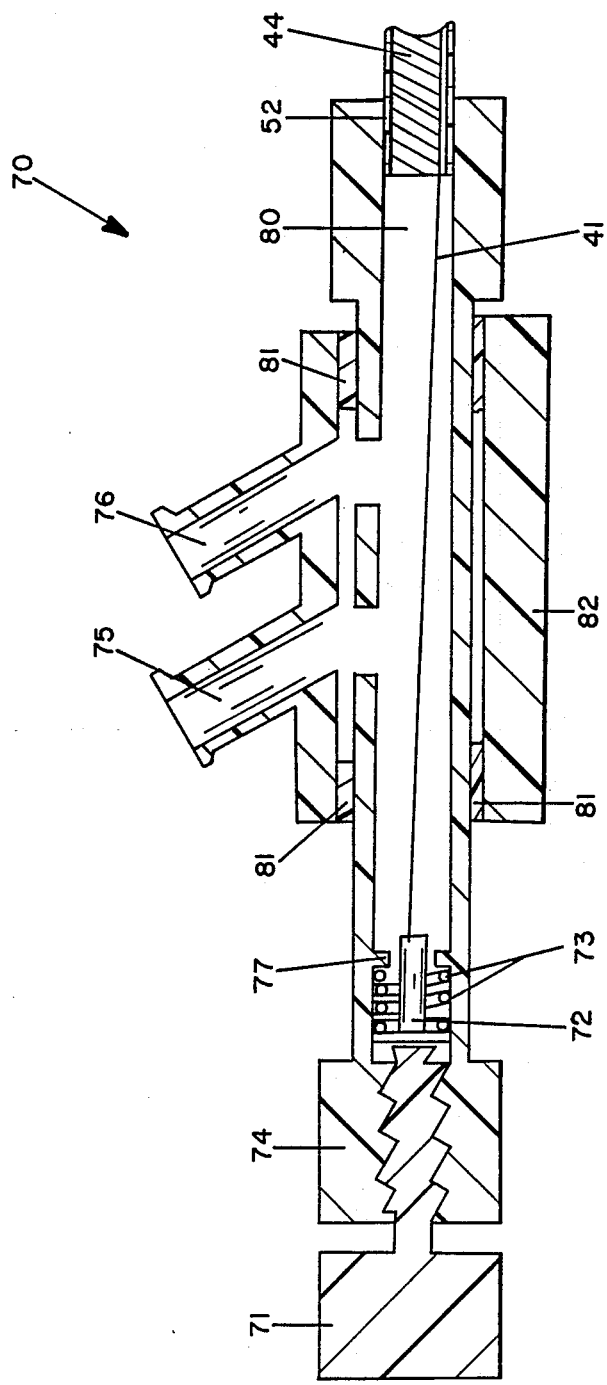
FIGS. 8 to 10 each represent a partly cross-sectional planar view of the proximal end of a catheter useful according to the invention.
Figure 9:
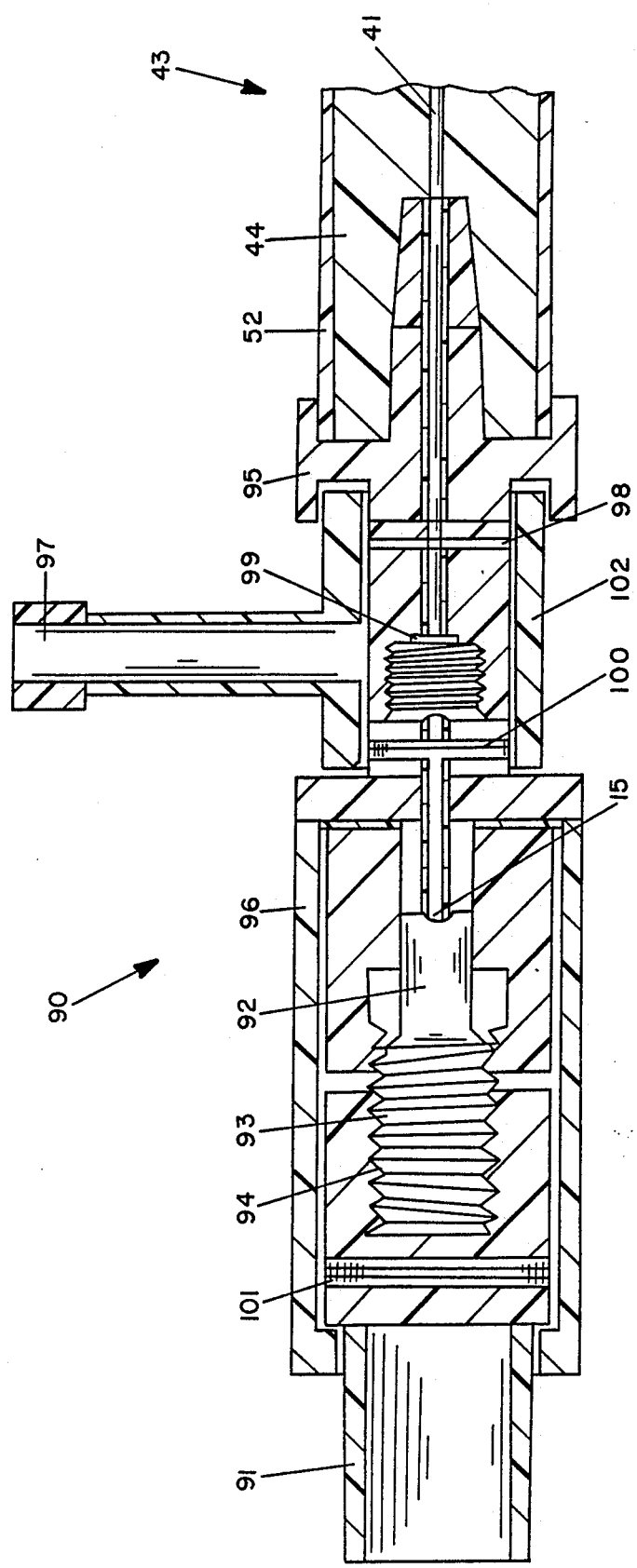
Figure 10:
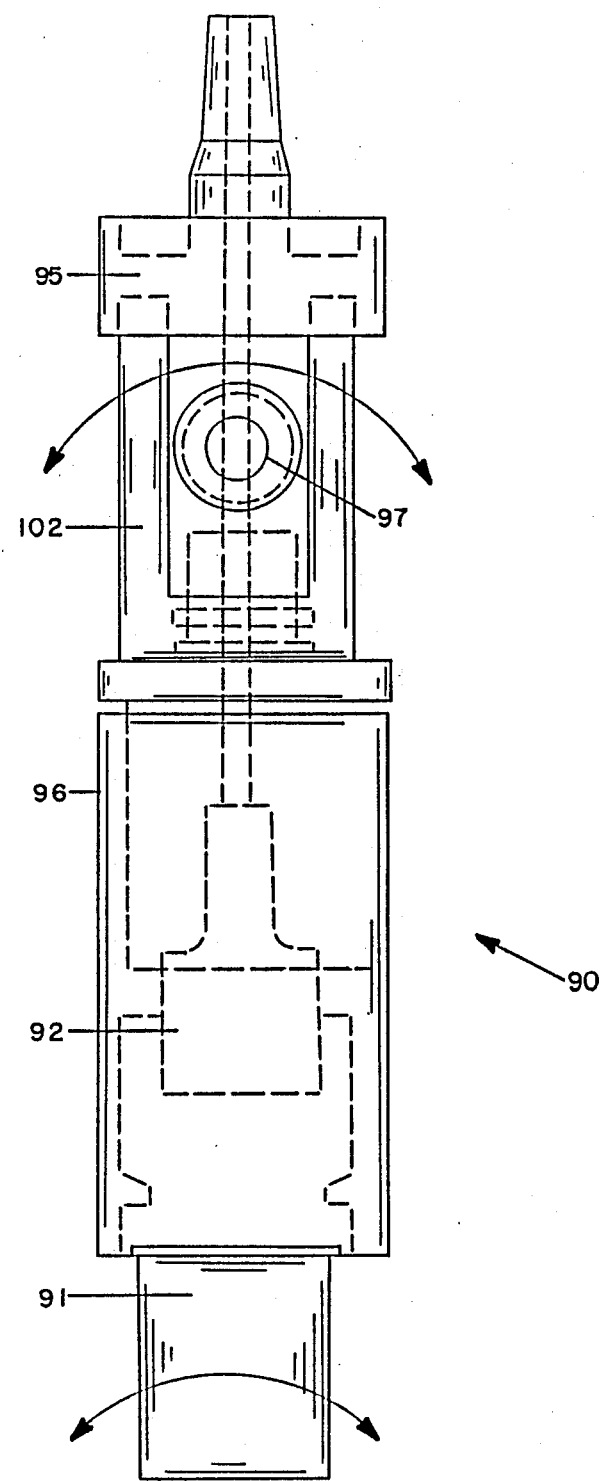

Alternate control means, generally designed as 70 and 90, are shown in FIGS. 8 to 10. Control means 70 employs a threaded or deflection knob 71 for precise tip deflection. Clockwise rotation of the deflection knob 71 causes pressure to be exerted on deflection wire termination block 72, which in turn causes pressure to be exerted distally along the longitudinal axis of deflection wire 41, which in turn causes the distal end of the catheter to deflect. When deflection knob 71 is backed out, i.e., rotated in counterclockwise fashion, a return spring 73 pushes the deflection wire termination block 72 back to its original position and thus allows the catheter tip to straighten. To rotate the catheter, rotation control knob 74 is rotated. This rotates the entire catheter body, i.e., body skin 52 and spring coil body 44, and the deflection wire 41 simultaneously.

The termination block 72 has a non-circular, e.g., rectangular or square, cross-section, and any rotational movement of the termination block is limited or prevented by substantially annular sealing/guide means 77. Preferably the only movement by the termination block 72 is in the longitudinal direction, i.e., proximally or distally.

Control means 70 also has ports 75 and 76 that are in fluid communication with a through-lumen 80, which is in turn in fluid communication with the lumen 54, for passage of liquids or other devices, e.g, other catheters, guidewires, pressure monitoring means, optical fibers, lasers, and the like, through the lumen 54. Annular seals 81, preferably made of suitable polymeric material such as TEFLON, allow the port section 82 to remain stationary while the rotation control knob 74 is manipulated.

As shown in FIGS. 9 and 10, control means 90 employs a threaded control or deflection knob 91 for precise tip deflection. The proximal end of the deflection wire 41 is fixedly engaged at engaging member 92, the outer surface of which has threading 93 which engages cooperating threading 94 on the inner surface of the distal portion of deflection knob 91. Rotation of deflection knob 91 causes movement of engaging member 92, which in turn causes movement of the deflection wire 41 along its longitudinal axis, which in turn causes the distal end of the catheter to deflect. The proximal end of catheter 43 is engagingly attached to attachment member 95, which is in turn connected to rotation control member 96. When rotation control member 96 is rotated, the catheter 43 is rotated, which in turn results in rotation of the distal end of the catheter 43.

Port 97 is in fluid communication with lumen 54 for inflation of the dilatation balloon (not shown). Annular seals 98, 99, 100, and 101 permit the port section 102 to remain stationery while the deflection knob 92 and/or the rotation control member 96 is manipulated.

In a variation of the control means shown in FIGS. 9 and 10, not shown, a control means comprises a deflection knob having an inflation port in fluid communication with lumen 54. This arrangement is advantageous in that fewer seals are required and the external source connecting to the inflation port is less in the way.

As discussed above, the outer sheath is slidable over each inner catheter. Such slidability is due either to the particular materials of which the outer sheath and each inner sheath are respectively comprised and/or any coating or treatment that may be applied to one or more surfaces. For example, the outer catheter and/or each inner catheter may be comprised of a suitable lubricous polymeric material, such as those selected from the group consisting of polyethylene, polyvinyl chloride, polypropylene, polytetrafluoroethylene, and copolymers thereof. In addition, the outer surface of an inner catheter and/or the inner surface of the outer sheath may have a coating thereon which promotes or facilitates slidability. Suitable such coatings, such as effective amounts of a material selected from the group consisting of hydrogels, silicones, and fluoropolymers such as polytetrafluoroethylene, are well known to those skilled in the art.

It is disclosed herein that an inner catheter may comprise one or more lumens. Advantageously such catheters comprise from one to four lumens, preferably from one to three lumens, and more preferably one or two lumens.

Figure 11:
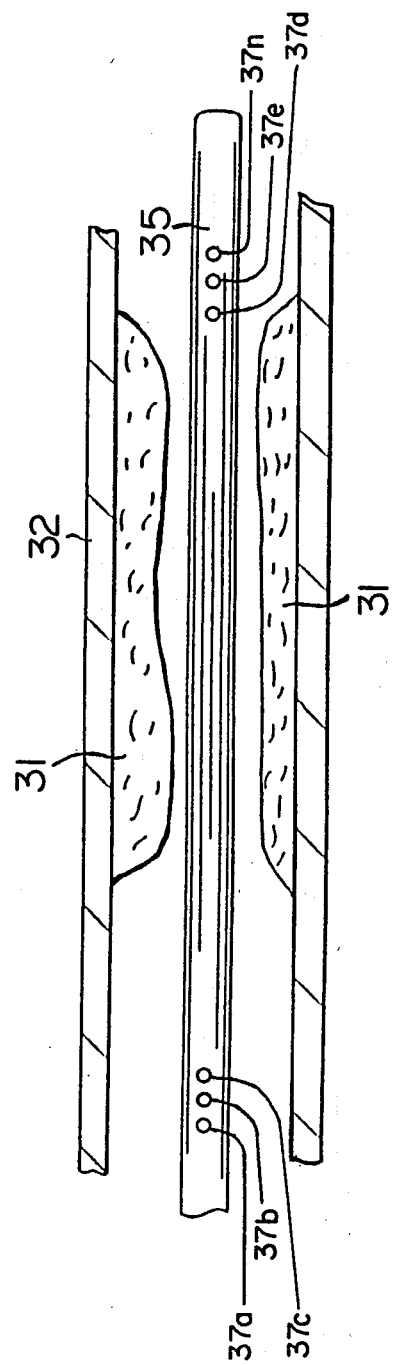
FIG. 11 is a close-up partially sectioned view of the distal tip of the inner catheter assembly showing the aperatures at the site of the occlusion.

As shown in FIG. 11, it is within the scope of the invention that the outer sheath may function as a shunt across a stenosis or blockage within an artery or other corporeal passageway. To facilitate such an arrangement the outer sheath would comprise small perforations 37a, 37b, through 37n or openings of suitable size and number to permit (i) entry into the outer sheath at a point proximal to the stenosis or blockage and (ii) exit from the sheath at a point distal to the stenosis or blockage. Said perforations, which would have to be of a small enough size and/or number that the structural integrity of the sheath would not be compromised, could be circular, oval, slotted, or the like. For example an arrangement of perforations could comprise from 3 to 10 equidistantly positioned circular holes of from 0.25 to 2.5 mm in diameter, around the circumference of the outer sheath.

The preceding specific embodiments are illustrative of the practice of the invention. It is to be understood, however, that other expedients known to those skilled in the art or disclosed herein, may be employed without departing from the spirit of the invention or the scope of the appended claims.

COMPONENT LIST

| No. | Component |
|---|---|
| 1 | catheter system |
| 2 | outer catheter sheath |
| 3 | inner catheter |
| 4 | deflection wire |
| 5 | control means |
| 6 | inner catheter distal end |
| 7 | outer sheath distal end |
| 8 | guidewire |
| 9 | distal end of guidewire |
| 10 | proximal end of guidewire |
| 15 | proximal end of deflection wire |
| 16 | engaging means |
| 20 | catheter system |
| 21 | outer sheath |
| 22 | inner catheter |
| 23 | control means |
| 24 | distal end of inner catheter |
| 25 | dilatation balloon |
| 27 | control knob |
| 28 | annular surface |
| 29 | inflation port |
| 30 | balloon dilatation catheter |
| 31 | stenosis |
| 33 | distal end of balloon dilatation catheter |
| 34 | dilatation balloon |
| 35 | outer sheath |
| 40 | tapered section of deflection wire |
| 41 | deflection wire |
| 42 | balloon section |
| 43 | catheter |
| 44 | spring coil body |
| 45 | closure |
| 46 | distal end of deflection wire |
| 47 | interior surface of distal end of spring coil body |
| 48 | safety wire |
| 49 | catheter distal tip |
| 50 | distal end of spring coil body |
| 51 | spring guide tip |
| 52 | tubing |
| 53 | space |
| 54 | lumen |
| 56 | body skin |
| 57 | distal end of spring coil body |
| 58 | spring coil body |
| 59 | atraumatic tip |
| 60 | liner |
| 61 | liner inner surface |
| 62 | deflection wire |
| 70 | control means |
| 71 | deflection knob |
| 72 | deflection wire termination block |
| 73 | return spring |
| 74 | rotation control knob |
| 75,76 | ports |
| 77 | guide means |
| 80 | through lumen |
| 81 | annular seal |
| 82 | port section |
| 90 | control means |
| 91 | deflection knob |
| 92 | engaging member |

-continued

| Component List | |
|---|---|
| No. | Component |
| 93,94 | threading |
| 95 | attachment member |
| 96 | rotation control member |
| 97 | port |
| 98, 99, 100, 101 | annular seals |
| 102 | port section |

We claim:

1. An outer exchange catheter system comprising an outer catheter sheath having a plurality of openings on the outer periphery wherein at least a first of said plurality of openings is positioned on said outer periphery at a point to permit fluid entry into said outer catheter sheath at a point proximal to a stenosis and at least a second of said plurality of openings is positioned on said outer periphery to permit fluid exit from said outer catheter sheath at a point distal to said stenosis and one or more inner catheters, at least one of which inner catheters comprises:
   a flexible catheter member having distal and proximal ends and one or more lumens extending therethrough, at least one of said lumens being closed at its distal end,
   a deflection wire having distal and proximal ends and extending the length of a lumen having a closed end, the distal end of the deflection wire being embedded in said closed end,
   control means attached to the proximal end of the catheter member, the proximal end of the deflection wire extending to the control means and the control means having an engaging means which fixedly engages said deflection wire, rotation of said engaging means causing the deflection wire to longitudinally displace either toward or away from the distal end of the catheter member, said displacement causing the distal end of the catheter member to bend out of or toward the line of the longitudinal axis of the catheter member, and the engaging means of the control means fixedly engaging the deflection wire so that when the control means is rotated, the catheter member and the deflection wire both rotate substantially together to cause the distal end of the catheter member to rotate about its longitudinal axis, and
   said outer catheter sheath extending less than the full length of each said inner catheter and being slidable thereover.

2. The catheter system of claim 1, wherein said outer catheter sheath extends from about 40% to 90% of the length of each said inner catheter 3. The catheter system of claim 1, wherein said outer catheter sheath and each said inner catheter have respective inner and outer surfaces and the inner surface of said outer catheter sheath and/or the outer surface of at least one said inner catheter has a coating thereon which promotes or facilitates slidability.

4. The catheter system of claim 1, wherein at least one of said outer catheter sheath and/or at least one said inner catheter is comprised of a polymeric substance having a low coefficient of friction.

5. An outer exchange catheter system comprising an outer catheter sheath and one or more inner catheters, wherein at least one of which inner catheters comprises:
   a flexible catheter member comprising a spring coil body defining a lumen, said spring coil body having proximal and distal ends, the distal end of said spring coil body being closed, and said spring coil body having a flexible covering thereon,
   dilatation balloon means positioned adjacent to the distal end of said spring coil body, and
   control means attached to the proximal end of said catheter member, so that when said control means is rotated, the catheter member rotates to cause the distal end of the catheter member to rotate about its longitudinal axis.

6. An outer exchange catheter system comprising an outer catheter sheath and one or more inner catheters, wherein at least one inner catheter comprises:
   a flexible catheter member comprising a spring coil body defining a lumen, said spring coil body having proximal and distal ends, the distal end of said spring coil body being open, and said spring coil body having a flexible covering thereon, and
   control means attached to the proximal end of said catheter member, so that when said control means is rotated, the catheter member rotates to cause the distal end of the catheter member to rotate about its longitudinal axis.

7. An outer exchange catheter system comprising an outer catheter sheath and one or more inner catheters, at least one of which inner catheters comprises:
   a flexible catheter member comprising a spring coil body defining a lumen, said spring coil body having proximal and distal ends, the distal end of said spring coil body being closed, and said spring coil body having a flexible covering thereon,
   dilatation balloon means positioned adjacent to the distal end of said spring coil body,
   a deflection wire having proximal and distal ends and being substantially co-extensive with said spring coil body, the distal end of said deflection wire being attached to the distal end of said spring coil body, and
   control means attached to the proximal end of said catheter member, the proximal end of said deflection wire extending to the control means, the control means having engaging means which fixedly engages the proximal end of said deflection wire, rotation of said engaging means causing the deflection wire to longitudinally displace either toward or away from the distal end of the catheter member, said displacement causing the distal end of the catheter member to bend out of or toward the line of the longitudinal axis of the catheter member, and the engaging means of the control means fixedly engaging the deflection wire so that when the control means is rotated, the catheter member and the deflection wire both rotate substantially together to cause the distal end of the catheter member to rotate about its longitudinal axis,
   said outer catheter sheath extending less than the full length of each said inner catheter and being slidable thereover.

8. The catheter system of claim 7, wherein said outer catheter sheath extends from about 40% to 90% of the length of each said inner catheter.

9. The catheter system of claim 7, wherein said outer catheter sheath and each said inner catheter have respective inner and outer surfaces and the inner surface of said outer catheter sheath and/or the outer surface of at least one said inner catheter have a coating thereon which promotes or facilitates slidability.

10. The catheter system of claim 7, wherein at least one of said outer catheter sheath and/or at least one said inner catheter is comprised of a polymeric substance having a low coefficient of friction.

11. The catheter system of claim 7, wherein at least one inner catheter comprises:
   a flexible catheter member comprising a spring coil body defining a lumen, said spring coil body having proximal and distal ends, the distal end of said spring coil body being closed, and said spring coil body having a flexible covering thereon,
   dilatation balloon means positioned adjacent to the distal end of said spring coil body, and
   control means attached to the proximal end of said catheter member, so that when said control means is rotated, the catheter member rotates to cause the distal end of the catheter member to rotate about its longitudinal axis.

12. The catheter member of claim 7, wherein at least one inner catheter member comprises:
   a flexible catheter member comprising a spring coil body defining a lumen, said spring coil body having proximal and distal ends, the distal end of said spring coil body being open, and said spring coil body having a flexible covering thereon, and
   control means attached to the proximal end of said catheter member, so that when said control means is rotated, the catheter member rotates to cause the distal end of the catheter member to rotate about its longitudinal axis.

13. An outer exchange catheter system comprising an outer catheter sheath and one or more inner catheters, at least one of which inner catheters comprises:
   a flexible catheter member comprising a spring coil body defining a lumen, said spring coil body having proximal and distal ends, a flexible tip having proximal and distal ends, the proximal end of said flexible tip being positioned distally a short distance from the distal end of said spring coil body to form a discontinuity, and a flexible covering, said flexible covering extending from the proximal end of said spring coil body along the length of said spring coil body across said discontinuity to the proximal end of said flexible tip,
   dilatation balloon means positioned around said discontinuity,
   a deflection wire having proximal and distal ends, said deflection wire extending substantially co-extensively with said spring coil body, the distal end of said deflection wire being attached to the proximal end of said flexible tip and
   control means having engaging means which fixedly engages the proximal end of said deflection wire, rotation of said engaging means causing the deflection wire to longitudinally displace either toward or away from the distal end of the catheter member, said displacement causing the distal end of the catheter member to bend out of or toward the line of the longitudinal axis of the catheter member, and the engaging means of the control means fixedly engaging the deflection wire so that when the control means is rotated, the catheter member and the deflection wire both rotate substantially together to cause the distal end of the catheter member to rotate about its longitudinal axis,
   said outer catheter sheath extending less than the full length of each said inner catheter and being slidable thereover.

14. The catheter system of claim 13, wherein said outer catheter sheath extends from about 40% to 90% of the length of each said inner catheter.

15. The catheter system of claim 13, wherein said outer catheter sheath and each said inner catheter have respective inner and outer surfaces and the inner surface of said outer catheter sheath and/or the outer surface of at least one said inner catheter have a coating thereon which promotes or facilitates slidability.

16. The catheter system of claim 13, wherein at least one of said outer catheter sheath and/or at least one said inner catheter is comprised of a polymeric substance having a low coefficient of friction.

17. The catheter system of claim 13, wherein at least one inner catheter comprises:
   a flexible catheter member comprising a spring coil body defining a lumen, said spring coil body having proximal and distal ends, the distal end of said spring coil body being closed, and said spring coil body having a flexible covering thereon,
   dilatation balloon means positioned adjacent to the distal end of said spring coil body and
   control means attached to the proximal end of said catheter member, so that when said control means is rotated, the catheter member rotates to cause the distal end of the catheter member to rotate about its longitudinal axis.

18. The catheter system of claim 13, wherein at least one inner catheter comprises:
   a flexible catheter member comprising a spring coil body defining a lumen, said spring coil body having proximal and distal ends, the distal end of said spring coil body being open, and said spring coil body having a flexible covering thereon, and
   control means attached to the proximal end of said catheter member, so that when said control is rotated, the catheter member rotates to cause the distal end of the catheter member to rotate about its longitudinal axis.

19. An outer exchange catheter system comprising an outer catheter sheath and one or more inner catheters, at least one of which inner catheters comprises:
   a flexible catheter member comprising a spring coil body defining a lumen, said spring coil body having proximal and distal ends, the distal end of said spring coil body being open,
   a deflection wire having proximal and distal ends and being substantially co-extensive with said spring coil body, the distal end of said deflection wire being attached to the distal end of said spring coil body, and
   control means attached to the proximal end of said catheter, the proximal end of said deflection wire extending through the control means, the control means having engaging means which fixedly engages the proximal end of said deflection wire, rotation of said engaging means causing the deflection wire to longitudinally displace either toward or away from the distal end of the catheter member, said displacement causing the distal end of the catheter member to bend out of or toward the line of the longitudinal axis of the catheter member, and the engaging means of the control means fixedly engaging the deflection wire so that when the control means is rotated, the catheter member and the deflection wire both rotate substantially together to cause the distal end of the catheter member to rotate about its longitudinal axis, said outer catheter sheath extending less than the full length of each said inner catheter and being slidable thereover.

20. The catheter system of claim 19, wherein said outer catheter sheath extends from about 40% to 90% of the length of each said inner catheter.

21. The catheter system of claim 19, wherein said outer catheter sheath and each said inner catheter have respective inner and outer surfaces and the inner surface of said outer catheter sheath and/or the outer surface of at least one said inner catheter have a coating thereon which promotes or facilitates slidability.

22. The catheter system of claim 19, wherein at least one of said outer catheter sheath and/or at least one said inner catheter is comprised of a polymeric substance having a low coefficient of friction.

23. The catheter system of claim 19, wherein at least one inner catheter comprises:
a flexible catheter member comprising a spring coil body defining a lumen, said spring coil body having proximal and distal ends, the distal end of said spring coil body being closed, and said spring coil body having a flexible covering thereon,
dilatation balloon means positioned adjacent to the distal end of said spring coil body, and
control means attached to the proximal end of said catheter member, so that when said control means is rotated, the catheter member rotates to cause the distal end of the catheter member to rotate about its longitudinal axis.

24. The catheter system of claim 19, wherein at least one inner catheter comprises:
a flexible catheter member comprising a spring coil body defining a lumen, said spring coil body having proximal and distal ends, the distal end of said spring coil body being open, and said spring coil body having a flexible covering thereon, and
control means attached to the proximal end of said catheter member, so that when said control means is rotated, the catheter member rotates to cause the distal end of the catheter member to rotate about its longitudinal axis.

25. A method for dilating a stenosis in a passageway in a body, which comprises:
(a) introducing a guide catheter having proximal and distal ends and a single lumen into the body through an incision or opening;
(b) advancing a catheter system comprising an outer sheath and a first inner dilatation catheter system, each of said outer sheath and said first dilatation catheter system having proximal and distal ends and said first dilatation catheter system having a first dilatation balloon means adjacent the distal end thereof, into and through the guide catheter to cause said first dilatation balloon means to be positioned across a stenosis in said passageway;
(c) inflating said first dilatation balloon means to cause the stenosis to dilate;
(d) deflating said first dilatation balloon means;
(e) withdrawing said first dilatation catheter system in the proximal direction;
(f) advancing a second dilatation catheter system having proximal and distal ends and second, larger dilatation balloon means distally within said outer sheath to cause the larger balloon dilatation means to be positioned across said stenosis;
(g) inflating said second balloon dilatation means; and
(h) repeating steps (d) to (g) until the stenosis is sufficiently dilated.

26. A method for dilating a stenosis in a passageway in a body, which comprises:
(a) introducing a guide catheter having proximal and distal ends and a single lumen into the body through an incision or opening;
(b) advancing a catheter system comprising an outer sheath and a first steerable inner dilatation catheter, each of said outer sheath and said first dilatation catheter having proximal and distal ends and said first dilatation catheter having first dilatation balloon means adjacent the distal end thereof, into and through the guide catheter to cause said first dilatation balloon means to be positioned across a stenosis in said passageway;
(c) inflating said first dilatation balloon means to cause the stenosis to dilate;
(d) deflating said first dilatation balloon means;
(e) slidably advancing the outer sheath distally along said first dilatation catheter to position said outer sheath across the stenosis;
(f) withdrawing said first dilatation catheter in the proximal direction;
(g) advancing a second dilatation catheter having proximal and distal ends and second, larger dilatation balloon means distally within said outer sheath to cause the larger balloon dilatation means to be positioned across said stenosis;
(h) withdrawing said outer sheath in the proximal direction to the extent that the outer sheath is no longer across the stenosis;
(i) inflating said second balloon dilatation means; and
(j) repeating steps (d) to (i) until the stenosis is sufficiently dilated.

27. The method of claim 26, wherein in step (h) the outer sheath is withdrawn to the extent that the proximal end of the outer sheath is positioned near the proximal end of the second dilatation catheter 28. The method of claim 26, wherein in step (h) the outer sheath is withdrawn to the extent that the distal end of the outer sheath is adjacent to the stenosis.

29. A method for dilating a stenosis in a passageway in a body, which comprises:
(a) introducing a guide catheter having proximal and distal ends and a single lumen into the body through an incision or opening;
(b) advancing a catheter system comprising an outer sheath and a guidewire, each of said outer sheath and said guidewire having proximal and distal ends, into and through the guide catheter to cause the distal ends of said outer sheath and said guidewire to be positioned proximally adjacent a stenosis in said passageway;
(c) advancing the distal end of said guidewire across the stenosis;
(d) advancing a balloon dilatation catheter system having a first balloon dilatation means over said guidewire to cause said first balloon dilatation means to be positioned across the stenosis;
(e) inflating said first dilatation balloon means to cause the stenosis to dilate;
(f) deflating said first dilatation balloon means;
(g) withdrawing said first dilatation catheter system in the proximal direction;
(h) advancing a second dilatation catheter system having proximal and distal ends and second, larger dilatation balloon means distally within said outer sheath and over said guidewire to cause the larger balloon dilatation means to be positioned across the stenosis;
(i) inflating said second balloon dilatation means; and
(j) repeating steps (d) to (i) until the stenosis is sufficiently dilated.

30. A method for dilating a stenosis in a passageway in a body, which comprises:
(a) introducing a guide catheter having proximal and distal ends and a single lumen into the body through an incision or opening;
(b) advancing a catheter system comprising an outer sheath and a guidewire, each of said outer sheath and said guidewire having proximal and distal ends, into and through the guide catheter to cause the distal ends of said outer sheath and said guidewire to be positioned proximally adjacent to a stenosis in said passageway;
(c) withdrawing said guidewire;
(d) advancing a first, fixed wire balloon dilatation catheter system having first balloon dilatation means adjacent the distal end thereof through the outer sheath and across the stenosis to cause said first balloon means to be positioned across the stenosis;
(e) inflating said first dilatation balloon means to cause the stenosis to dilate;
(f) deflating said first dilatation balloon means;
(g) withdrawing said first dilatation catheter in the proximal direction;
(h) advancing a second dilatation catheter having proximal and distal ends and second, larger dilatation balloon means distally within said outer sheath to cause the second balloon dilatation means to be positioned across said stenosis;
(i) inflating said second balloon dilatation means; and
(j) repeating steps (d) to (i) until the stenosis is sufficiently dilated.

31. A method for dilating a stenosis in a passageway in a body, which comprises:
(a) introducing a guide catheter having proximal and distal ends and a single lumen into the body through an incision or opening;
(b) advancing a catheter system comprising an outer sheath and a guidewire, each of said outer sheath and said guidewire having proximal and distal ends, into and through the guide catheter to cause the distal ends of said outer sheath and said guidewire to be positioned proximally adjacent to a stenosis in said passageway;
(c) withdrawing said guidewire;
(d) advancing a first fixed wire balloon dilatation catheter system having first balloon dilatation means adjacent the distal end thereof through the outer sheath and across the stenosis to cause said first balloon dilatation means to be positioned across the stenosis;
(e) inflating said first dilatation balloon means to cause the stenosis to dilate;
(f) deflating said first dilatation balloon means;
(g) slidably advancing the outer sheath distally along said first dilatation catheter to position said outer sheath across the stenosis;
(h) withdrawing said first dilatation catheter in the proximal direction;
(i) advancing a second dilatation catheter having proximal and distal ends and second, larger dilatation balloon means distally within said outer sheath to cause the larger balloon dilatation means to be positioned across the stenosis;
(j) withdrawing said outer sheath in the proximal direction to the extent that the outer sheath is no longer across the stenosis;
(k) inflating said second balloon dilatation means; and
(l) repeating steps (d) to (k) until the stenosis is sufficiently dilated.

32. The method of claim 31, wherein in step (j) the outer sheath is withdrawn to the extent that the proximal end of the outer sheath is positioned near the proximal end of the second dilatation catheter 33. The method of claim 31, wherein in step (j) the outer sheath is withdrawn to the extent that the distal end of the outer sheath is proximally adjacent to the stenosis.

* * * * *